United States Patent [19]

Hamon et al.

[11] Patent Number: 5,510,331

[45] Date of Patent: Apr. 23, 1996

[54] ANTIHYPERTENSIVE PEPTIDES

[75] Inventors: Gilles Hamon, Le Raincy; Eve Mahe; Dung Le-Nguyen, both of Montpellier, all of France

[73] Assignee: Roussel UCLAF, France

[21] Appl. No.: 322,707

[22] Filed: Oct. 13, 1994

Related U.S. Application Data

[63] Continuation of Ser. No. 795,426, Nov. 20, 1991, abandoned.

[30] Foreign Application Priority Data

Nov. 21, 1990 [FR] France .................... 90 14498

[51] Int. Cl.⁶ .................... A61K 35/34; A61K 38/39; C07K 14/435
[52] U.S. Cl. ................ 514/13; 514/9; 514/930; 530/326
[58] Field of Search ............... 530/326; 514/13, 514/930, 9

[56] References Cited

U.S. PATENT DOCUMENTS 4,981,950  1/1991  Masaki et al. .................... 514/13

FOREIGN PATENT DOCUMENTS 0402313  12/1990  European Pat. Off. .

OTHER PUBLICATIONS

Nakajima et al. Biochem/Biophys Res. Comm vol. 163, No. 1, pp. 424–429 (1989).

*Primary Examiner*—Christina Y. Chan
*Assistant Examiner*—Lynn Touzeau
*Attorney, Agent, or Firm*—Bierman and Muserlain

[57] ABSTRACT

Peptides of the formula $$R_1-HX_1\ DX_2\ IX_3 \qquad I$$

wherein $R_1$, $X_1$, $X_2$ and $X_3$ are defined as in the specification having antihypertensive activity without vasoconstricting activity.

3 Claims, No Drawings

SEQUENCE LISTING ( 1 ) GENERAL INFORMATION:

( i i i ) NUMBER OF SEQUENCES: 27

( 2 ) INFORMATION FOR SEQ ID NO: 1:

( i ) SEQUENCE CHARACTERISTICS:
      ( A ) LENGTH: 7
      ( B ) TYPE: Amino acid
      ( C ) STRANDEDNESS: Single
      ( D ) TOPOLOGY: Unknown ( i i ) MOLECULE TYPE: Peptide ( i x ) FEATURE:
      ( B ) LOCATION: 1
      ( D ) OTHER INFORMATION: Xaa is peptide of Seq. 2

( i x ) FEATURE:
      ( B ) LOCATION: 3
      ( D ) OTHER INFORMATION: Xaa is residue of
         Leu, Arg, or Gln ( i x ) FEATURE:
      ( B ) LOCATION: 5
      ( D ) OTHER INFORMATION: Xaa is residue of
         Ile or Val ( i x ) FEATURE:
      ( B ) LOCATION: 7
      ( D ) OTHER INFORMATION: Xaa is residue of
         Trp, Amidotryptophan or D-naphthylalanine ( x i ) SEQUENCE DESCRIPTION:SEQ ID NO: 1:

Xaa His Xaa Asp Xaa Ile Xaa
 1               5

( 2 ) INFORMATION FOR SEQ ID NO: 2:

( i ) SEQUENCE CHARACTERISTICS:
      ( A ) LENGTH: 15
      ( B ) TYPE: Amino acid
      ( C ) STRANDEDNESS: Single
      ( D ) TOPOLOGY: Unknown ( i i ) MOLECULE TYPE: Peptide ( i x ) FEATURE:
      ( B ) LOCATION: 7
      ( D ) OTHER INFORMATION: Xaa is residue of Nle, Gly,
         Val, Ile, Leu, Ala, Phe, Beta-alanine, or Met ( i x ) FEATURE:

(B) LOCATION: 12
(D) OTHER INFORMATION: Xaa is residue of
Val, Leu, or Glu EXCEPT Xaa (7) is not Met
when Xaa(12) is Val or Xaa(1) of Seq. 1 is
= Seq. 3.

(ix) FEATURE:
(D) OTHER INFORMATION: Optional disulfide bridges:
Cys (1) and Cys (15); Cys (3) and Cys (11).

(xi) SEQUENCE DESCRIPTION:SEQ ID NO: 2:

| Cys | Ser | Cys | Ser | Ser | Leu | Xaa | Asp | Lys | Glu | Cys | Xaa | Tyr | Phe | Cys |
|---|---|---|---|---|---|---|---|---|---|---|---|---|---|---|
| 1 | | | | 5 | | | | | 10 | | | | | 15 |

(2) INFORMATION FOR SEQ ID NO: 3:

(i) SEQUENCE CHARACTERISTICS:
(A) LENGTH: 15
(B) TYPE: Amino acid
(C) STRANDEDNESS: Single
(D) TOPOLOGY: Unknown (ii) MOLECULE TYPE: Peptide (ix) FEATURE:
(B) LOCATION: 12
(D) OTHER INFORMATION: Xaa is residue of
Leu or Val EXCEPT Xaa (12) is not Leu
when Xaa(2) of Seq. 1 is Gln or Xaa(1) of
Seq. 1 is Seq. 4 or Seq. 5.

(ix) FEATURE:
(D) OTHER INFORMATION: Optional disulfide bridges:
Cys (1) and Cys (15); Cys (3) and Cys (11).

(xi) SEQUENCE DESCRIPTION:SEQ ID NO: 3:

| Cys | Thr | Cys | Lys | Asp | Met | Thr | Asp | Lys | Glu | Cys | Xaa | Tyr | Phe | Cys |
|---|---|---|---|---|---|---|---|---|---|---|---|---|---|---|
| 1 | | | | 5 | | | | | 10 | | | | | 15 |

(2) INFORMATION FOR SEQ ID NO: 4:

(i) SEQUENCE CHARACTERISTICS:
(A) LENGTH: 9
(B) TYPE: Amino acid
(C) STRANDEDNESS: Single
(D) TOPOLOGY: Unknown (ii) MOLECULE TYPE: Peptide (ix) FEATURE:
(B) LOCATION: 5
(D) OTHER INFORMATION: Xaa is Nle.

(ix) FEATURE:
(D) OTHER INFORMATION: Optional disulfide bridge:
Cys (1) and Cys (9).

(xi) SEQUENCE DESCRIPTION:SEQ ID NO: 4:

| Cys | Ser | Ser | Leu | Xaa | Asp | Lys | Glu | Cys |
|---|---|---|---|---|---|---|---|---|
| 1 | | | | 5 | | | | |

(2) INFORMATION FOR SEQ ID NO: 5:

(i) SEQUENCE CHARACTERISTICS:
(A) LENGTH: 9
(B) TYPE: Amino acid
(C) STRANDEDNESS: Single
(D) TOPOLOGY: Unknown (ii) MOLECULE TYPE: Peptide (ix) FEATURE:
(B) LOCATION: 1
(D) OTHER INFORMATION: Xaa is residue of Cys or Ala or Ser.

( i x ) FEATURE:
  ( B ) LOCATION: 9
  ( D ) OTHER INFORMATION: Xaa is residue of
    Cys or Ala or Ser.

( i x ) FEATURE:
  ( D ) OTHER INFORMATION: Optional disulfide
    bridge at Xaa (1) and Xaa (9) when they
    are Cys.

( x i ) SEQUENCE DESCRIPTION:SEQ ID NO: 5:

Xaa  Leu  Ala  Gly  Pro  Asn  Gly  Tyr  Xaa
 1                     5

( 2 ) INFORMATION FOR SEQ ID NO: 6:

( i ) SEQUENCE CHARACTERISTICS:
    ( A ) LENGTH: 7
    ( B ) TYPE: Amino acid
    ( C ) STRANDEDNESS: Single
    ( D ) TOPOLOGY: Unknown ( i i ) MOLECULE TYPE: Peptide ( i x ) FEATURE:
    ( B ) LOCATION: 1
    ( D ) OTHER INFORMATION: Xaa is peptide of
      Seq. 2.

( i x ) FEATURE:
    ( B ) LOCATION: 3
    ( D ) OTHER INFORMATION: Xaa is residue of
      Leu or Arg or Glu.

( i x ) FEATURE:
    ( B ) LOCATION: 5
    ( D ) OTHER INFORMATION: Xaa is Ile residue.

( i x ) FEATURE:
    ( B ) LOCATION: 7
    ( D ) OTHER INFORMATION: Xaa is residue of
      Trp, Amidotryptophan, D-naphthyl-alanine.

( x i ) SEQUENCE DESCRIPTION:SEQ ID NO: 6:

Xaa  His  Xaa  Asp  Xaa  Ile  Xaa
 1              5

( 2 ) INFORMATION FOR SEQ ID NO: 7:

( i ) SEQUENCE CHARACTERISTICS:
    ( A ) LENGTH: 7
    ( B ) TYPE: Amino acid
    ( C ) STRANDEDNESS: Single
    ( D ) TOPOLOGY: Unknown ( i i ) MOLECULE TYPE: Peptide ( i x ) FEATURE:
    ( B ) LOCATION: 1
    ( D ) OTHER INFORMATION: Xaa is peptide of
      Seq. 8 or Seq. 9.

( i x ) FEATURE:
    ( B ) LOCATION: 3
    ( D ) OTHER INFORMATION: Xaa is residue of
      Leu or Arg or Glu.

( i x ) FEATURE:
    ( B ) LOCATION: 5
    ( D ) OTHER INFORMATION: Xaa is residue of
      Ile or Val.

( i x ) FEATURE:
    ( B ) LOCATION: 7

(D) OTHER INFORMATION: Xaa is residue of
Trp or Amidotryptophan or D-naphthylalanine.

(x i) SEQUENCE DESCRIPTION:SEQ ID NO: 7:

Xaa His Xaa Asp Xaa Ile Xaa
 1                5

(2) INFORMATION FOR SEQ ID NO: 8:

(i) SEQUENCE CHARACTERISTICS:
       (A) LENGTH: 15
       (B) TYPE: Amino acid
       (C) STRANDEDNESS: Single
       (D) TOPOLOGY: Unknown (i i) MOLECULE TYPE: Peptide (i x) FEATURE:
       (B) LOCATION: 7
       (D) OTHER INFORMATION: Xaa is residue of
           Gly or Val or Beta-alanine.

(i x) FEATURE:
       (B) LOCATION: 12
       (D) OTHER INFORMATION: Xaa is residue of
           Val or Leu.

(i x) FEATURE:
       (D) OTHER INFORMATION: Optional disulfide bridge:
           Cys (3) and Cys (11).

(x i) SEQUENCE DESCRIPTION:SEQ ID NO: 8:

Cys Ser Cys Ser Ser Leu Xaa Asp Lys Glu Cys Xaa Tyr Phe Cys
 1               5                   10                  15

(2) INFORMATION FOR SEQ ID NO: 9:

(i) SEQUENCE CHARACTERISTICS:
       (A) LENGTH: 15
       (B) TYPE: Amino acid
       (C) STRANDEDNESS: Single
       (D) TOPOLOGY: Unknown (i i) MOLECULE TYPE: Peptide (i x) FEATURE:
       (B) LOCATION: 12
       (D) OTHER INFORMATION: Xaa is residue of
           Val or Leu.

(i x) FEATURE:
       (D) OTHER INFORMATION: Optional disulfide bridge:
           Cys (9) and Cys (11).

(x i) SEQUENCE DESCRIPTION:SEQ ID NO: 9:

Cys Thr Cys Lys Asp Met Thr Asp Lys Glu Cys Xaa Tyr Phe Cys
 1               5                   10                  15

(2) INFORMATION FOR SEQ ID NO: 10:

(i) SEQUENCE CHARACTERISTICS:
       (A) LENGTH: 21
       (B) TYPE: Amino acid
       (C) STRANDEDNESS: Single
       (D) TOPOLOGY: Unknown (i i) MOLECULE TYPE: Peptide (i x) FEATURE:
       (B) LOCATION: 7
       (D) OTHER INFORMATION: Xaa is Nle.

(i x) FEATURE:
       (D) OTHER INFORMATION: Optional disulfide bridges:

Cys (1) and Cys (15); Cys (3) and Cys (11).

( x i ) SEQUENCE DESCRIPTION:SEQ ID NO: 10:

Cys Ser Cys Ser Ser Leu Xaa Asp Lys Glu Cys Val Tyr Phe Cys
1               5                   10                  15
His Leu Asp Ile Ile Trp
                    20

( 2 ) INFORMATION FOR SEQ ID NO: 11:

( i ) SEQUENCE CHARACTERISTICS:
        ( A ) LENGTH: 21
        ( B ) TYPE: Amino acid
        ( C ) STRANDEDNESS: Single
        ( D ) TOPOLOGY: Unknown ( i i ) MOLECULE TYPE: Peptide ( i x ) FEATURE:
        ( D ) OTHER INFORMATION: Optional disulfide bridges:
            Cys (1) and Cys (15); Cys (3) and Cys (11).

( x i ) SEQUENCE DESCRIPTION:SEQ ID NO: 11:

Cys Ser Cys Ser Ser Leu Gly Asp Lys Glu Cys Val Tyr Phe Cys
1               5                   10                  15
His Leu Asp Ile Ile Trp
                    20

( 2 ) INFORMATION FOR SEQ ID NO: 12:

( i ) SEQUENCE CHARACTERISTICS:
        ( A ) LENGTH: 21
        ( B ) TYPE: Amino acid
        ( C ) STRANDEDNESS: Single
        ( D ) TOPOLOGY: Unknown ( i i ) MOLECULE TYPE: Peptide ( i x ) FEATURE:
        ( D ) OTHER INFORMATION: Optional disulfide bridges:
            Cys (1) and Cys (15); Cys (3) and Cys (11).

( x i ) SEQUENCE DESCRIPTION:SEQ ID NO: 12:

Cys Thr Cys Lys Asp Met Thr Asp Lys Glu Cys Leu Tyr Phe Cys
1               5                   10                  15
His Arg Asp Ile Ile Trp
                    20

( 2 ) INFORMATION FOR SEQ ID NO: 13:

( i ) SEQUENCE CHARACTERISTICS:
        ( A ) LENGTH: 7
        ( B ) TYPE: Amino acid
        ( C ) STRANDEDNESS: Single
        ( D ) TOPOLOGY: Unknown ( i i ) MOLECULE TYPE: Peptide ( i x ) FEATURE:
        ( B ) LOCATION: 1
        ( D ) OTHER INFORMATION: Xaa is peptide of
            Seq. 4 or Seq. 5 where Xaa (1 and 9)
            are Cys residues.

( i x ) FEATURE:
        ( B ) LOCATION: 3
        ( D ) OTHER INFORMATION: Xaa is residue of
            Leu, Arg or Gln.

( i x ) FEATURE:
        ( B ) LOCATION: 5

(D) OTHER INFORMATION: Xaa is residue of
Ile or Val.

(ix) FEATURE:
(B) LOCATION: 7
(D) OTHER INFORMATION: Xaa is residue of
Trp, Amidotryptophan or D-Naphthylalanine.

(xi) SEQUENCE DESCRIPTION:SEQ ID NO: 13:

Xaa His Xaa Asp Xaa Ile Xaa
 1               5

(2) INFORMATION FOR SEQ ID NO: 14:

(i) SEQUENCE CHARACTERISTICS:
(A) LENGTH: 21
(B) TYPE: Amino acid
(C) STRANDEDNESS: Single
(D) TOPOLOGY: Unknown (ii) MOLECULE TYPE: Peptide (ix) FEATURE:
(D) OTHER INFORMATION: Optional disulfide bridges:
Cys (1) and Cys (15); Cys (3) and Cys (11).

(xi) SEQUENCE DESCRIPTION:SEQ ID NO: 14:

Cys Ser Cys Ser Ser Leu Met Asp Lys Glu Cys Val Tyr Phe Cys
 1               5                   10                  15
His Leu Asp Ile Ile Trp
                 20

(2) INFORMATION FOR SEQ ID NO: 15:

(i) SEQUENCE CHARACTERISTICS:
(A) LENGTH: 21
(B) TYPE: Amino acid
(C) STRANDEDNESS: Single
(D) TOPOLOGY: Unknown (ii) MOLECULE TYPE: Peptide (ix) FEATURE:
(B) LOCATION: 7
(D) OTHER INFORMATION: Xaa is Nle.

(ix) FEATURE:
(B) LOCATION: 21
(D) OTHER INFORMATION: Xaa is D- Naphthylalanine.

(xi) SEQUENCE DESCRIPTION:SEQ ID NO: 15:

Cys Ser Cys Ser Ser Leu Xaa Asp Lys Glu Cys Val Tyr Phe Cys
 1               5                   10                  15
His Leu Asp Ile Ile Xaa
                 20

(2) INFORMATION FOR SEQ ID NO: 16:

(i) SEQUENCE CHARACTERISTICS:
(A) LENGTH: 21
(B) TYPE: Amino acid
(C) STRANDEDNESS: Single
(D) TOPOLOGY: Unknown (ii) MOLECULE TYPE: Peptide (ix) FEATURE:
(B) LOCATION: 7
(D) OTHER INFORMATION: Xaa is Nle.

(ix) FEATURE:
(B) LOCATION: 21

( D ) OTHER INFORMATION: Xaa is Amidotryptophan.

( x i ) SEQUENCE DESCRIPTION:SEQ ID NO: 16:

Cys Ser Cys Ser Ser Leu Xaa Asp Lys Glu Cys Val Tyr Phe Cys
1               5                   10                  15

His Leu Asp Ile Ile Xaa
20

( 2 ) INFORMATION FOR SEQ ID NO: 17:

( i ) SEQUENCE CHARACTERISTICS:
        ( A ) LENGTH: 21
        ( B ) TYPE: Amino acid
        ( C ) STRANDEDNESS: Single
        ( D ) TOPOLOGY: Unknown ( i i ) MOLECULE TYPE: Peptide ( i x ) FEATURE:
        ( B ) LOCATION: 7
        ( D ) OTHER INFORMATION: Xaa is Beta- alanine.

( x i ) SEQUENCE DESCRIPTION:SEQ ID NO: 17:

Cys Ser Cys Ser Ser Leu Xaa Asp Lys Glu Cys Val Tyr Phe Cys
1               5                   10                  15

His Leu Asp Ile Ile Trp
                20

( 2 ) INFORMATION FOR SEQ ID NO: 18:

( i ) SEQUENCE CHARACTERISTICS:
        ( A ) LENGTH: 21
        ( B ) TYPE: Amino acid
        ( C ) STRANDEDNESS: Single
        ( D ) TOPOLOGY: Unknown ( i i ) MOLECULE TYPE: Peptide ( x i ) SEQUENCE DESCRIPTION:SEQ ID NO: 18:

Cys Ser Cys Ser Ser Leu Val Asp Lys Glu Cys Val Tyr Phe Cys
1               5                   10                  15

His Leu Asp Ile Ile Trp
                20

( 2 ) INFORMATION FOR SEQ ID NO: 19:

( i ) SEQUENCE CHARACTERISTICS:
        ( A ) LENGTH: 15
        ( B ) TYPE: Amino acid
        ( C ) STRANDEDNESS: Single
        ( D ) TOPOLOGY: Unknown ( i i ) MOLECULE TYPE: Peptide ( i x ) FEATURE:
        ( B ) LOCATION: 5
        ( D ) OTHER INFORMATION: Xaa is Nle.
            Disulfide bridge: Cys (1) and
            Cys (9).

( x i ) SEQUENCE DESCRIPTION:SEQ ID NO: 19:

Cys Ser Ser Leu Xaa Asp Lys Glu Cys His Leu Asp Ile Ile Trp
1               5                   10                  15

( 2 ) INFORMATION FOR SEQ ID NO: 20:

( i ) SEQUENCE CHARACTERISTICS:
        ( A ) LENGTH: 15
        ( B ) TYPE: Amino acid ( C ) STRANDEDNESS: Single
( D ) TOPOLOGY: Unknown ( i i ) MOLECULE TYPE: Peptide ( i x ) FEATURE:
( B ) LOCATION: 5
( D ) OTHER INFORMATION: Xaa is Nle.

( x i ) SEQUENCE DESCRIPTION:SEQ ID NO: 20:

Cys Ser Ser Leu Xaa Asp Lys Glu Cys His Leu Asp Ile Ile Trp
1               5                   10                  15

( 2 ) INFORMATION FOR SEQ ID NO: 21:

( i ) SEQUENCE CHARACTERISTICS:
( A ) LENGTH: 15
( B ) TYPE: Amino acid
( C ) STRANDEDNESS: Single
( D ) TOPOLOGY: Unknown ( i i ) MOLECULE TYPE: Peptide ( i x ) FEATURE:
( D ) OTHER INFORMATION: Disulfide
bridge: Cys (1) and Cys (9).

( x i ) SEQUENCE DESCRIPTION:SEQ ID NO: 21:

Cys Leu Ala Gly Pro Asn Gly Tyr Cys His Leu Asp Ile Ile Trp
1               5                   10                  15

( 2 ) INFORMATION FOR SEQ ID NO: 22:

( i ) SEQUENCE CHARACTERISTICS:
( A ) LENGTH: 15
( B ) TYPE: Amino acid
( C ) STRANDEDNESS: Single
( D ) TOPOLOGY: Unknown ( i i ) MOLECULE TYPE: Peptide ( x i ) SEQUENCE DESCRIPTION:SEQ ID NO: 22:

Cys Leu Ala Gly Pro Asn Gly Tyr Cys His Leu Asp Ile Ile Trp
1               5                   10                  15

( 2 ) INFORMATION FOR SEQ ID NO: 23:

( i ) SEQUENCE CHARACTERISTICS:
( A ) LENGTH: 21
( B ) TYPE: Amino acid
( C ) STRANDEDNESS: Single
( D ) TOPOLOGY: Unknown ( i i ) MOLECULE TYPE: Peptide ( i x ) FEATURE:
( D ) OTHER INFORMATION: Disulfide bridges:
Cys (1) and Cys (15); Cys (3) and
Cys (11).

( x i ) SEQUENCE DESCRIPTION:SEQ ID NO: 23:

Cys Thr Cys Lys Asp Met Thr Asp Lys Glu Cys Val Tyr Phe Cys
1               5                   10                  15

His Leu Asp Ile Ile Trp
                20

( 2 ) INFORMATION FOR SEQ ID NO: 24:

( i ) SEQUENCE CHARACTERISTICS:
( A ) LENGTH: 21
( B ) TYPE: Amino acid (C) STRANDEDNESS: Single
(D) TOPOLOGY: Unknown (ii) MOLECULE TYPE: Peptide (ix) FEATURE:
  (B) LOCATION: 7
  (D) OTHER INFORMATION: Xaa is Nle.
      Disulfide bridges: Cys (1) and
      Cys (15); Cys (3) and Cys (11).

(xi) SEQUENCE DESCRIPTION:SEQ ID NO: 24:

| Cys | Ser | Cys | Ser | Ser | Leu | Xaa | Asp | Lys | Glu | Cys | Val | Tyr | Phe | Cys |
|---|---|---|---|---|---|---|---|---|---|---|---|---|---|---|
| 1 | | | | 5 | | | | | 10 | | | | | 15 |

| His | Gln | Asp | Ile | Ile | Trp |
|---|---|---|---|---|---|
| | | | | 20 | |

(2) INFORMATION FOR SEQ ID NO: 25:

(i) SEQUENCE CHARACTERISTICS:
    (A) LENGTH: 21
    (B) TYPE: Amino acid
    (C) STRANDEDNESS: Single
    (D) TOPOLOGY: Unknown (ii) MOLECULE TYPE: Peptide (ix) FEATURE:
    (D) OTHER INFORMATION: Disulfide bridges:
        Cys (1) and Cys (15); Cys (3) and
        Cys (11).

(xi) SEQUENCE DESCRIPTION:SEQ ID NO: 25:

| Cys | Ser | Cys | Ser | Ser | Leu | Met | Asp | Lys | Glu | Cys | Leu | Tyr | Phe | Cys |
|---|---|---|---|---|---|---|---|---|---|---|---|---|---|---|
| 1 | | | | 5 | | | | | 10 | | | | | 15 |

| His | Gln | Asp | Ile | Ile | Trp |
|---|---|---|---|---|---|
| | | | | 20 | |

(2) INFORMATION FOR SEQ ID NO: 26:

(i) SEQUENCE CHARACTERISTICS:
    (A) LENGTH: 15
    (B) TYPE: Amino acid
    (C) STRANDEDNESS: Single
    (D) TOPOLOGY: Unknown (ii) MOLECULE TYPE: Peptide (ix) FEATURE:
    (B) LOCATION: 13
    (D) OTHER INFORMATION: Xaa is Ile
        or Val.

(xi) SEQUENCE DESCRIPTION:SEQ ID NO: 26:

| Ala | Leu | Ala | Gly | Pro | Asn | Gly | Tyr | Ala | His | Leu | Asp | Xaa | Ile | Trp |
|---|---|---|---|---|---|---|---|---|---|---|---|---|---|---|
| 1 | | | | 5 | | | | | 10 | | | | | 15 |

(2) INFORMATION FOR SEQ ID NO: 27:

(i) SEQUENCE CHARACTERISTICS:
    (A) LENGTH: 21
    (B) TYPE: Amino acid
    (C) STRANDEDNESS: Single
    (D) TOPOLOGY: Unknown (ii) MOLECULE TYPE: Peptide (xi) SEQUENCE DESCRIPTION:SEQ ID NO: 27:

| Cys | Thr | Cys | Lys | Asp | Met | Thr | Asp | Lys | Glu | Cys | Leu | Tyr | Phe | Cys |
|---|---|---|---|---|---|---|---|---|---|---|---|---|---|---|
| 1 | | | | 5 | | | | | 10 | | | | | 15 |

His Arg Asp Ile Ile Trp
                    20

ANTIHYPERTENSIVE PEPTIDES

This application is a continuation of U.S. patent application Ser. No. 795,426 filed Nov. 20, 1991, now abandoned.

Endotheline is a powerful vasoconstrictor extracted from porcine aortic endothelium and this peptide which has been recently isolated comprises 21 amino acids, has 2 disulfide bridges and has the formula (SEQ ID NO. 14):

```
C S C S S L M D K E C V Y F C H L D I I W
1     5       10      15      20
```

A novel potent vasoconstrictor peptide produced by vascular endothelial cells taught by Yanagisawa et al, Nature, (1988), Vol. 332, p. 411–415 is designated in what follows under the name of ET1. The nomenclature used is that of the IUPAC-IUB commission (1984) European J. Biochem., Vol. 183, pg. 9–37. This peptide which contains 21 amino-acid residues and 2 disulfide bridges is capable of contracting the smooth muscle cells (arteries and veins) of different species of mammals (man, dog, cat, pig, guinea-pig, rat, rabbit . . . ) at very low doses. Other prior art includes FEBS Letters, Vol. 256, No. 1 (Oct. 2, 1989), pg. 1 to 3 and Biochemical and Biophysical Research, Vol. 163, No. 1 (Aug. 30, 1989), pg. 424–429.

OBJECT OF THE INVENTION

It is an object of the invention to provide novel peptides by shortening the chain of endotheline and replacing certain amino acids with other amino acids in which the vascoconstricting activity of endotheline is avoided while retaining the property of blocking and fixing itself on the natural receptors of endotheline.

It is another object of the invention to provide novel antihypertensive compositions and a novel method of inducing antihypertensive activity in warm-blooded animals.

These and other objects and advantages of the invention will become obvious from the following detailed description.

THE INVENTION

The novel peptides of the invention have the formula (SEQ ID NO. 1)

$$R_1-HX_1DX_2IX_3 \quad \quad I$$

wherein $X_1$ is the residue of leucine or arginine or glutamine, $X_2$ is the residue of isoleucine or valine, $X_3$ is a residue of tryptophan or amidotryptophan or D-naphthylalanine and $R_1$ is a remainder of 15 amino-acids of the formula (SEQ ID NO. 2)

```
                                        Ia
C S C S S L X4 D K E C X5 Y F C—
1     5       10
```

$X_4$ in 7-position is a residue of an amino acid selected from the group consisting of glycine, nor-leucine, valine, isoleucine, leucine, alanine, phenylalanine, beta-alanine and methionine, $X_5$ in 12-position is a residue of valine or leucine or glutamic acid and the broken line represents an optional disulfide bridge between two cysteine residues with the proviso that $X_4$ is not methionine residue when $X_5$ is a valine residue or $R_1$ is the remainder of 15 amino acids of the formula (SEQ ID NO. 3)

```
                                        Ib
C T C K D M T D K E C X6 Y F C—
1     5       10
```

$X_6$ is a residue of leucine or valine and the broken line is an optional disulfide bridge between 2 cysteine residues with the proviso that $X_6$ is not a leucine residue when $X_1$ is a glutamine residue or $R_1$ is remainder of 9 amino acids of the formula (SEQ ID NO. 4)

```
                                        Ic
C S S L X7 D K E C—
1     5
```

$X_7$ in 5-position is a nor-leucine residue and the broken line is an optional disulfide bridge between 2 cysteine residues or $R_1$ is a remainder of 9 amino acids of the formula (SEQ ID NO. 5)

```
                                        Id
X8 L A G P N G Y X8—
1     5
```

$X_8$ is a residue of cysteine or alanine or serine and the broken line is an optional disulfide bridge between 2 cysteine residues.

A preferred group of the peptides of the invention are those wherein $X_1$ is a residue of leucine, arginine or glutamine, $X_2$ is an isoleucine residue and $X_3$ is a residue of tryptophan, amidotryptophan or D-naphthylalanine. Among the latter, preferably are those wherein $R_1$ is a remainder of the amino-acids of formula Ia, $X_4$ in 7-position is a residue of glycine, valine or beta-alanine and $X_5$ in 12-position is a residue of valine or leucine and the broken line optionally is a disulfide bridge between 2 cysteine residues or $R_1$ is a remainder of the 15 amino-acids of Formula Ib, $X_6$ is a residue of leucine or valine, and the broken line optionally is a disulfide bridge between 2 cysteine residues.

Also preferred are those wherein $R_1$ is a remainder of the 9 amino-acids of formula Ic, $X_7$ in 5-position is a nor-leucine residue and the broken line optionally is a disulfide bridge between 2 cysteine residues, or $R_1$ is a remainder of the 9 amino-acids of formula Id, $X_8$ is a cysteine residue and the broken line optionally is a disulfide bridge between 2 cysteine residues.

Especially preferred peptides are those of the formulae

```
                                        (SEQ ID NO. 10)
C S C S S L Nle D K E C V Y F C H L D I I W,
1     5       10      15      20
```

```
                                        (SEQ ID NO. 11)
C S C S S L G D K E C V Y F C H L D I I W and
1     5       10      15      20
```

```
                                        (SEQ ID NO. 12)
C T C K D M T D K E C L Y F C H R D I I W
1     5       10      15      20
```

The novel process of the invention for the preparation of the peptides of the invention comprises forming a solid phase by sequentially introducing protected amino acids onto a cross-linked polystyrene resin type support with a coupling agent, deprotecting the amino acids, releasing the peptide chain from the support and optionally cyclizing the disulfide bridge(s).

In a preferred mode of the process of the invention, the cross-linked polystyrene type is Boc—Trp—CM type where Boc is tert-butoxycarbonyl, Trp is a tryptophyl and CM is the cross-linked polystyrene support, the coupling agent is Bop or (benzotriazol-1-yloxy)-tris(dimethylamino)-phosphonium hexafluorophosphate and the deprotection of the amino acids and release from the support is effected with hydrofluoric acid at low temperatures, especially at about 0° C.

The novel antihypertensive compositions of the invention are comprised of an antihypertensively effective amount of at least one novel peptide of the invention and an inert pharmaceutical carrier or excipient. The compositions may be in the form of tablets, dragees, gelules, capsules, granules, suppositories, aerosols and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions have a remarkable inhibiting effect against hypertension induced by endotheline and an antischemic activity without the vasoconstricting activity of endotheline. The compositions are useful in the treatment of all vascular spasms, in the treatment of post-brain hemorrhages, in the treatment of coronary spasms and peripheral vascular spasms and renal insufficiency.

The novel method of the invention for inducing antihypertensive activity in warm-blooded animals, including humans, comprises administering to warm-blooded animals an antihypertensively effective amount of a peptide of formula I. The peptide can be administered orally, rectally or parenterally and the usual daily dose is 0.013 to 4 mg/kg depending on the condition treated, the method of administration and the specific peptide.

In the following examples, there are described several preferred embodiments to illustrate the invention. However, it should be understood that the invention is not intended to be limited to the specific embodiments.

EXAMPLE 1

[Nle-7]—ET1 Derivative

STAGE A: Assembly of the Peptide Chain

A "Boc—Trp—CM—support" type support was used in which Boc is a tert-butoxycarbonyl, Trp is a tryptophyl and CM-support is a cross-linked polystyrene support. The support containing 0.6 mmol Trp/g was prepared by the potassium fluoride method of Horiki et al (1978) Chemistry Lett., pg. 165–168. All the amino-acids were N-protected by tert-butylcarbonyl. The protector groups of the lateral chains were p-methyl benzyl for cysteine, cyclohexyl ester for aspartic acid and glutamic acid, benzyl for serine, o-chlorobenzyloxycarbonyl for lysine, 2,6-dichlorobenzyl for tyrosine, Nim-tertiobutyloxycarbonyl, tryptophan and methionine were not protected.

The coupling reactions were carried out using Bop or (benzotriazol-1-yloxy)-tris(dimethylamino)-phosphonium hexafluorophosphate). A coupling cycle can be summarized as follows:

Deprotection

1. Treatment with a 50% solution of trifluoroacetic acid in dichloromethane containing 3% of ethanedithiol for 1 minute.

2. Draining, then treatment with a 50% solution of trifluoroacetic acid in dichloromethane containing 3% of ethanedithiol for 30 minutes.

3. Draining, then washing with isopropanol containing 5% of ethanedithiol.

4. Washing with dichloromethane, twice.

Coupling

1. Addition of Bop and Boc-amino acid.

2. Addition of diisopropylethylamine (6 equivalents), then of solvent (dichloromethane or dimethylformamide) with stirring.

3. After a negative reaction to ninhydrin, washing twice with dichloromethane.

Control tests using ninhydrin were carried out following the process described by Kaiser et al, (1970) Anal. Biochem., Vol. 24, pg. 595–598. Before treatment with hydrofluoric acid, the last group of Boc was eliminated with trifluoroacetic acid. From 2 g of "Boc—Trp—CM—resin" type resin, 5.25 g of protected peptide chain-resin complex was obtained by operating manually, which was used directly for the following step.

STEP B: Release of the Protected Peptide Chain—Resin Complex 1.5 g of protected peptide chain-resin complex were reacted for 60 minutes with 15 ml of hydrofluoric acid at 0° C. in the presence of 1 ml of anisole and 0.5 ml of dimethylsulfide. The resin was washed with ether and the crude peptide was extracted with an aqueous solution of acetic acid at 20%. After lyophilization, 660 mg of non-cyclized crude product were obtained which were used directly for the following step.

STEP C: Cyclization and Purification 500 mg of the crude peptide of Step B were dissolved in 250 ml of water and the solution was vigorously stirred while diisopropyl ethylamine was added until a pH of 8 was obtained. A drop of mixture was collected every hour and added to a drop of a solution containing dithiobis (2-nitrobenzoic) acid in a molar buffer of $K_2HPO_4$ (pH 8) to monitor the oxidation reaction. During the reaction, the pH was kept at 8 by the addition of diisopropylethylamine. The reaction was followed by high performance liquid chromatography (HPLC). After 28 hours, the absence of yellow coloration was observed in the test using dithiobis (2-nitrobenzoic) acid.

The product obtained was purified by high performance liquid chromatography (HPLC) on a M20 $ODS_3$ Whatman column and eluted with a water-acetonitrile mixture containing 0.1% trifluoroacetic acid. The fraction was lyophilized to obtain 30 mg of the expected product whose amino-acid composition appears in Table I.

EXAMPLES 2 TO 15

Using the procedure of Example 1 but with other amino-acids, 14 other micro-proteins were prepared which appear hereafter. However, for the products of Examples 2 to 15, at Step C of cyclization and purification, 500 ml of water per 500 mg of peptide were used.

EXAMPLE 2

(Gly-7)—ET1 derivative (SEQ ID NO. 11)

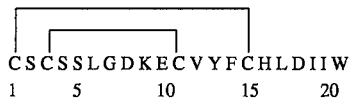

```
C S C S S L G D K E C V Y F C H L D I I W
1       5         10        15        20
```

EXAMPLE 3

(Nle-7)-DiNaphtylalanine-21-ET1 derivative.

EXAMPLE 4

(Nle-7)-Amidotryptophan-21-ET1 derivative.

EXAMPLE 5

(Beta-alanine-7)-ET1 derivative.

EXAMPLE 6

(Val-7)-ET1 derivative.

EXAMPLE 7

Derivative of formula Ic ($X_7$=Nle, $X_1$=Leu, $X_2$= Ile, $X_3$=Trp with disulfide bridge between cysteines 1 and 9).

EXAMPLE 8

Derivative of Formula Ic ($X_7$= Nle, $X_1$=Leu, $X_2$= Ile, $X_3$ =Trp without disulfide bridge between cysteines 1 and 9).

EXAMPLE 9

Derivative of Formula Id ($X_8$ in position 1 and 9= Cys, $X_1$=Leu, $X_2$=Ile, $X_3$=Trp with disulfide bridge between cysteines 1 and 9).

EXAMPLE 10

Derivative of Formula Id ($X_8$ in position 1 and 9= Cys, $X_1$=Leu, $X_2$=Ile, $X_3$=Trp without disulfide bridge between cysteines 1 and 9).

EXAMPLE 11

Derivative of Formula Ib ($X_6$ in position 12=Val, $X_1$=Leu, $X_2$=Ile, $X_3$=Trp with two disulfide bridges between cysteines 1–15 and 3–11).

EXAMPLE 12

Derivative of Formula Ia ($X_4$ in position 7=Nle, $X_1$=Gln, $X_2$=Ile, $X_3$=Trp, $X_5$=Val with two disulfide bridges between cysteines 1–15 and 3–11).

EXAMPLE 13

Derivative of Formula Ia ($X_4$ in position 7=Met, $X_5$ in position 12=Leu, $X_1$=Gln, $X_2$=Ile, $X_3$=Trp with two disulfide bridges between cysteines 1–15 and 3–11).

EXAMPLE 14

Derivative of Formula Id ($X_8$ in position 1 and 9=Ala, $X_1$=Leu, $X_3$=Trp).

EXAMPLE 15

Derivative of Formula Ib ($X_6$=Leu, $X_1$=Arg, $X_2$=Ile, $X_3$=Trp).

The amino-acid compositions are indicated in Table I.

TABLE I

|     | 2   | 3   | 4   | 5   | 6   | 7   | 8   | 9   | 10  | 11  | 12  | 13  | 14  |
| --- | --- | --- | --- | --- | --- | --- | --- | --- | --- | --- | --- | --- | --- |
| Asp | 2,2 | 1,8 | 1,9 | 2,2 | 1,9 | 2,1 | 1,9 | 2,1 | 1,9 | 2,9 | 2,2 | 2,1 | 1,8 |
| Glu | 1,1 | 1,1 | 1,2 | 1,2 | 0,9 | 0,8 | 0,9 | —   | —   | 0,9 | 1,9 | 1,8 | —   |
| Ser | 3,1 | 3,3 | 3,1 | 3,3 | 3,3 | 1,9 | 1,8 | —   | —   | —   | 3,1 | 3,1 | —   |
| Gly | 1,1 | 0   | 0   | 0   | 0,8 | 0   | —   | 1,8 | 1,9 | —   | —   | —   | 2,1 |
| His | 0,9 | 1,1 | 1,2 | 1,2 | 0   | 0,8 | 0,9 | 1,1 | 0,9 | 1,1 | 1,1 | 1,1 | 1,1 |
| Arg | 0   | 0   | 0   | 0   | 0   | 0   | —   | —   | —   | —   | —   | —   | —   |
| Thr | 0   | 0   | 0   | 0   | 0   | 0   | —   | —   | —   | 2,1 | —   | —   | —   |
| Ala | 0   | 0   | 0   | 0   | 0   | 0   | —   | 0,9 | 1,1 | —   | —   | —   | 3,1 |
| Pro | 0   | 0   | 0   | 0   | 0   | 0   | —   | —   | —   | —   | —   | —   | —   |
| Tyr | 0,8 | 0,9 | 1,8 | 0,9 | 0,9 | 0   | —   | 0,9 | 0,8 | 0,8 | 0,9 | 0,8 | 0,9 |
| Val | 1,2 | 1,2 | 1,1 | 1,2 | 2,2 | 0   | —   | —   | —   | 1,1 | 0,9 | —   | —   |
| Met | 0   | 0   | 0   | 0   | 0   | 0   | —   | —   | —   | 0,7 | —   | 0,8 | —   |
| Cys | 1,5 | 0,1 | 0,2 | 1,4 | 1,3 | 0,3 | 0,5 | 0,6 | 0,4 | 1,1 | 0,9 | 1,1 | —   |
| Ile | 2,1 | 2,1 | 2,2 | 2,1 | 1,9 | 2,2 | 2,1 | 2,2 | 2,1 | 1,9 | 1,9 | 1,8 | 2,2 |
| Leu | 1,9 | 3,1 | 3,2 | 2,1 | 2,1 | 3,1 | 3,2 | 2,1 | 1,9 | 0,9 | 3,1 | 3,2 | 1,9 |
| Phe | 0,9 | 0,8 | 0,9 | 0,9 | 1,1 | 0   | —   | —   | —   | 0,9 | 1,1 | 1,1 | —   |
| Lys | 1,1 | 0,9 | 1,1 | 1,1 | 0,9 | 0   | —   | —   | —   | 1,8 | 1,1 | 0,9 | —   |

EXAMPLE 16

An injectable solute was prepared comprising 1 mg of the product of Example 1 and sufficient sterile aqueous excipient for a solution of 2 ml.

EXAMPLE 17

Tablets were prepared containing 2 mg of the product of Example 1 and excipient of lactose, starch, talc and magnesium stearate for a final weight of 150 mg.

STUDY OF THE ACTIVITY ON THE ENDOTHELINE RECEPTOR

A membrane preparation was made from rat posterior cortex and brain and the tissue was ground with a POLYTRON in a 50 mM Tris buffer pH=7.4. After 30 minutes at 25° C. (W.B.), the homogenate was centrifuged at 30,000 g for 15 minutes (2 centrifugations with intermediate taking up in the Tris buffer pH 7.4). The deposits were suspended in an incubation buffer (Tris 25 mM, pepstatine A 5 microg/ml, aprotinine 3 microg/ml, PMSF 0.1 mM, EDTA 3 mM, EGTA 1 mM pH 7.4). 2 ml aliquots were distributed in hemolysis tubes and $^{125}$I endotheline (approximately 50,000 dpm/tube) and the product to be studied were added. The product was first tested at $3\times10^{-5}$M in triplicate. When the product tested displaced more than 50% of radioactivity linked specifically to the receptor, it was tested again in a range of 7 concentrations to determine the concentration which inhibited the radioactivity linked specifically to the receptor by 50%. In this way, the 50% inhibiting concentration was determined.

The non-specific bond was determined by the addition of endotheline at $10^{-6}$M (in triplicate) and the deposits were incubated at 25° C. for 60 minutes, put in a water-bath at 0° C. for 5 minutes, filtered under reduced pressure and rinsed with a Tris buffer 7.4 pH. The radioactivity was counted in the presence of scintillating Triton. The result was expressed directly as a 50% inhibiting concentration (IC50), or the concentration of product studied expressed in nM necessary to displace 50% of the specific radioactivity fixed on the receptor studied.

Result:

The IC50-s found for the products of Examples 1 to 15 are given in Table II in nanomoles.

TABLE II

| PRODUCTS OF EXAMPLES | IC50 (nM) |
| --- | --- |
| 1 | 10 |
| 2 | 1.4 |
| 3 | 2 |
| 4 | 10 |
| 5 | 2.5 |
| 6 | 5.2 |
| 7 | 3520 |
| 8 | 5350 |
| 9 | 7500 |
| 10 | 620 |

TABLE II-continued

| PRODUCTS OF EXAMPLES | IC50 (nM) |
| --- | --- |
| 11 | 1.3 |
| 12 | 2.3 |
| 13 | 3.5 |
| 14 | 6200 |
| 15 | 1.8 |

Various modifications of the products and method of the invention may be made without departing from the spirit or scope thereof and it is to be understood that the invention is intended to be limited only as defined in the appended claims.

---

What is claimed is:

1. A peptide selected from the group consisting of (SEQ ID NO. 10)

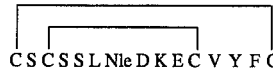

C S C S S L Nle D K E C V Y F C H L D I I W,
1       5         10        15       20

(SEQ ID NO. 11)

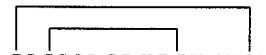

C S C S S L G D K E C V Y F C H L D I I W and
1       5         10        15       20

(SEQ ID NO. 12)

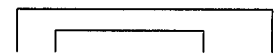

C T C K D M T D K E C L Y F C H R D I I W.
1       5         10        15       20

2. An antihypertensive composition comprising an antihypertensively effective amount of a peptide of claim 1 and an inert pharmaceutical carrier.

3. A method of inducing antihypertensive activity in warm-blooded animals comprising administering to warm-blooded animals an antihypertensively effective amount of a peptide of claim 1.

* * * * *